(12) United States Patent
Obrachta

(10) Patent No.: US 7,552,641 B2
(45) Date of Patent: Jun. 30, 2009

(54) THROUGH-TRANSMISSION ULTRASONIC INSPECTION SYSTEM AND TESTING METHODS

(75) Inventor: Kevin L. Obrachta, Wichita, KS (US)

(73) Assignee: The Boeing Company, Chicago, IL (US)

(*) Notice: Subject to any disclaimer, the term of this patent is extended or adjusted under 35 U.S.C. 154(b) by 0 days.

(21) Appl. No.: 11/765,376

(22) Filed: Jun. 19, 2007

(65) Prior Publication Data

US 2008/0034874 A1 Feb. 14, 2008

Related U.S. Application Data

(62) Division of application No. 11/001,317, filed on Nov. 30, 2004, now Pat. No. 7,249,514.

(51) Int. Cl.
*G01N 29/28* (2006.01)
(52) U.S. Cl. .......................................... 73/644; 73/627
(58) Field of Classification Search .................... 73/644, 73/598, 629
See application file for complete search history.

(56) References Cited

U.S. PATENT DOCUMENTS

| | | | |
|---|---|---|---|
| 5,001,932 A | | 3/1991 | Light et al. |
| 5,522,878 A | * | 6/1996 | Montecalvo et al. ........ 600/459 |
| 5,684,252 A | | 11/1997 | Kessler et al. |
| 5,736,470 A | | 4/1998 | Schneberger et al. |
| 6,085,591 A | | 7/2000 | Mallard |
| 6,591,680 B2 | | 7/2003 | Batzinger et al. |
| 2003/0087201 A1 | | 5/2003 | Wu |
| 2004/0044298 A1 | * | 3/2004 | Kawabata et al. ............... 601/2 |
| 2006/0106311 A1 | * | 5/2006 | Lo et al. ..................... 600/459 |

* cited by examiner

*Primary Examiner*—Hezron Williams
*Assistant Examiner*—Rose M Miller
(74) *Attorney, Agent, or Firm*—Hope Baldauff Hartman, LLC

(57) ABSTRACT

Methods and systems are provided for protecting an acoustic liner having a perforated facesheet from water leakage during a through-transmission ultrasonic (TTU) inspection using an ultrasonic squirter system. The testing method utilizes a repositionable mask that covers the openings in the perforated facesheet. The repositionable mask utilizes a pressure sensitive adhesive that adheres to the surface of the perforated facesheet. The repositionable mask can be removed after completing a TTU inspection and can be reused for subsequent TTU tests with minimal adverse effects on the mask or on the facesheet. For ease in handling, the repositionable mask may be configured with a semi-rigid backing carrier.

20 Claims, 3 Drawing Sheets ize the noise
THROUGH-TRANSMISSION ULTRASONIC INSPECTION SYSTEM AND TESTING METHODS

CROSS-REFERENCE TO RELATED APPLICATION

This application is a divisional of U.S. patent application Ser. No. 11/001,317, filed Nov. 30, 2004, now U.S. Pat. No. 7,249,514.

TECHNICAL FIELD

The present invention generally relates to through-transmission ultrasonic (TTU) inspection, and more particularly relates to a repositionable mask, a testing system, and testing methods that are used to protect the article being TTU inspected.

BACKGROUND

Acoustic liners are generally used to suppress sound propagation from a noisy source. In the aerospace industry, for example, acoustic liners are often used to reduce the noise emanating from an aircraft engine and fan assembly. Typically, the aircraft engine and fan are housed within a nacelle enclosure, and acoustic liners are generally integrated within the nacelle structure. While acoustic liners can be fabricated from metal or composite materials, composites offer a number of advantages, such as weight reduction and improved fatigue resistance in a high sonic environment, among others. Composite acoustic liners are typically fabricated in a sandwich-type configuration, with a solid backsheet, a honeycomb sound-absorbing core middle section, and a perforated facesheet.

Composite acoustic liners for this type of noise suppression application are generally inspected by an ultrasonic technique, such as a "through-transmission ultrasonic" (TTU) process. One type of TTU inspection procedure, known as an ultrasonic squirter system, utilizes water streams that are directed against the outside surfaces of the article being inspected, in order to carry the ultrasonic inspection signal from an ultrasonic transmitter through the test article to an ultrasonic receiver. In the case of a composite acoustic liner TTU inspection, the perforated facesheet on the acoustic liner is generally masked with some type of taping material to prevent water from entering the honeycomb structure through the facesheet perforations, since the presence of water in the honeycomb structure can cause problems in the subsequent finish and assembly operations. After completing a TTU inspection, the masking material is typically removed manually, and discarded. For applications involving relatively large test articles, such as aircraft nacelle acoustic liners, the manual taping and tape removal processes can be labor-intensive, and may also result in the deposit of masking material residue on the acoustic liner surface, leading to a possible degradation in performance of the acoustic liner.

Accordingly, it is desirable to provide a mask for TTU squirter system inspection of an acoustic liner that is relatively easy to apply and relatively easy to remove, and that does not deposit residue on the surface being masked. In addition, it is desirable to provide a mask that can be repositioned (i.e., reused) for subsequent ultrasonic testing. Furthermore, other desirable features and characteristics of the present invention will become apparent from the subsequent detailed description and the appended claims, taken in conjunction with the accompanying drawings and the foregoing technical field and background.

BRIEF SUMMARY

According to various exemplary embodiments, devices and methods are provided for protecting one or more surfaces of an article from water while the article is undergoing squirter system through-transmission ultrasonic (TTU) inspection. One embodiment comprises a repositionable mask in the form of a pressure sensitive adhesive layer configured to adhere to the one or more surfaces of the article. The pressure sensitive adhesive layer is also configured to be removable from the one or more surfaces of the article after completion of squirter system TTU inspection. Moreover, the removed pressure sensitive adhesive layer can be reused for protecting other article surfaces during subsequent squirter system TTU inspections.

An exemplary embodiment of the repositionable mask is typically fabricated from an ethylene vinyl acetate copolymer with approximately 50% vinyl acetate content to provide the desired adhesion characteristics. An alternate embodiment of the repositionable mask can be configured with a backing material carrier integrated with the pressure sensitive adhesive layer. The backing material carrier is typically configured as a semi-rigid pre-contoured carrier, and is generally fabricated from thermoformed acrylic or from thermoformed polycarbonate.

BRIEF DESCRIPTION OF THE DRAWINGS

The present invention will hereinafter be described in conjunction with the following drawing figures, wherein like numerals denote like elements.

DETAILED DESCRIPTION

The following detailed description is merely exemplary in nature and is not intended to limit the invention or the application and uses of the invention. Furthermore, there is no intention to be bound by any expressed or implied theory presented in the preceding technical field, background, brief summary or the following detailed description.

Various embodiments of the present invention pertain to the area of through-transmission ultrasonic (TTU) squirter system inspection of articles susceptible to water intrusion, such as acoustic liners with perforated facesheets and honeycomb interiors. To protect this type of article during a TTU squirter system inspection, a mask is typically applied to the water-susceptible surface(s) to prevent water dispensed by the ultrasonic squirter system from entering the article interior (honeycomb section). The exemplary mask to be described below is typically fabricated from a pressure sensitive adhesive that is relatively easy to apply and also relatively easy to remove. The exemplary mask is designated herein as a "repositionable" mask because it can generally be removed intact from a test article surface, and then reused for subsequent TTU inspections.

Figure 1:
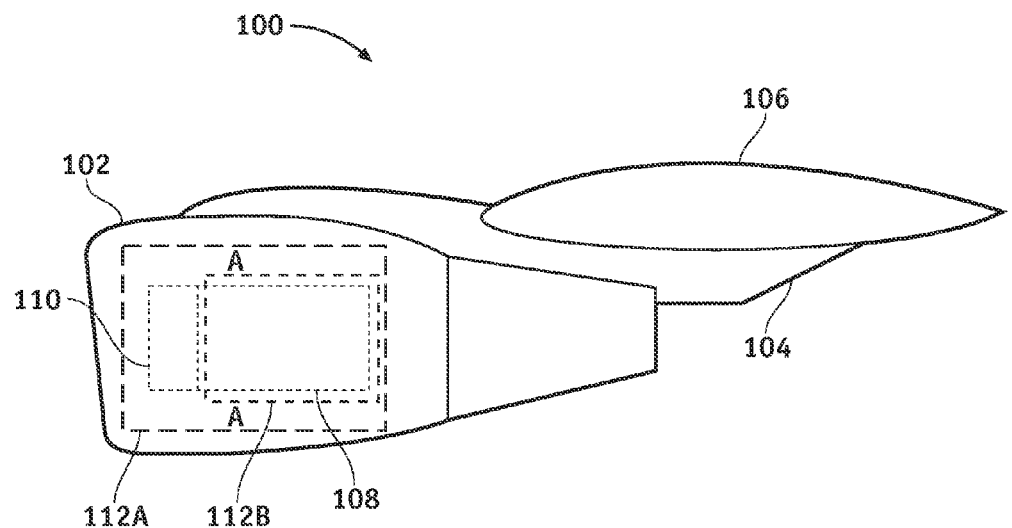
FIG. 1 is a simplified illustration of an exemplary aircraft engine pod configuration.

As noted in the Background, acoustic liners are commonly used to suppress the noise emanating from an aircraft engine and fan assembly, as well as other associated noise-generating components. A simplified illustration of an aircraft engine pod configuration 100 is shown in FIG. 1. In this example, a nacelle 102 is attached via a strut 104 to a wing 106. Nacelle 102 typically encloses an engine 108, an engine fan 110, and an acoustic liner arrangement 112A, 112B. Depending on the type and location of noise suppression desired, an acoustic liner arrangement can be configured in various forms, and is typically integrated into the structure of nacelle 102. For example, the acoustic liner configuration shown in FIG. 1 includes an outer duct wall 112A with a perforated facesheet on the "inner" surface facing engine 108 and fan 110, and an inner duct wall 112B surrounding engine 108 with a perforated facesheet on the "outer" surface facing outer duct wall 112A. This type of acoustic liner arrangement is typically designed to suppress noise in area A that is largely generated by engine 108 and air flow from fan 110, which may be running at a speed in the approximate range of six thousand (6,000) RPM.

Figure 2:
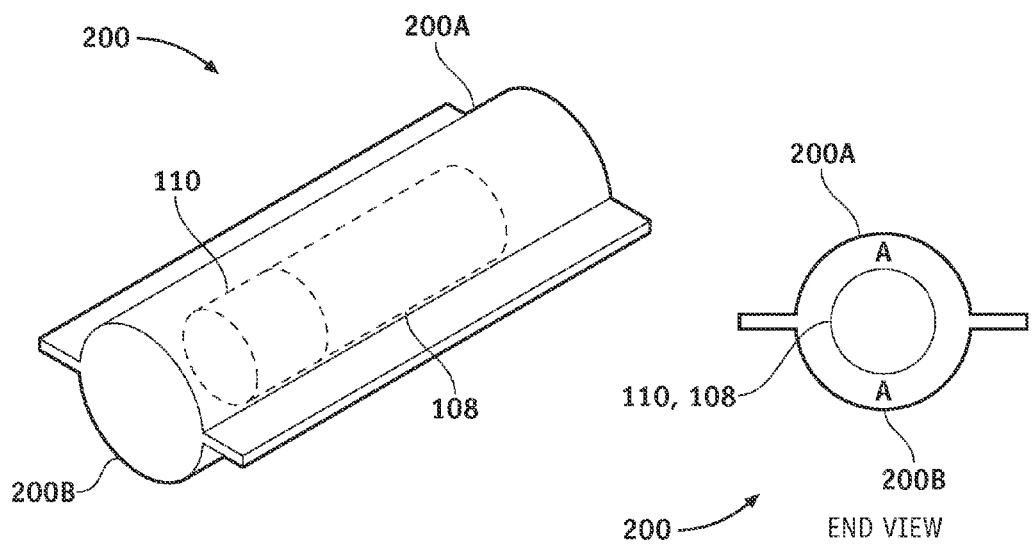
FIG. 2 is an illustration of an exemplary acoustic liner for an aircraft engine nacelle.

An exemplary configuration of an acoustic liner 200 (e.g., outer duct wall 112A in FIG. 1) is illustrated in the isometric and end views of FIG. 2. In this configuration, acoustic liner 200 is fabricated in two parts, 200A and 200B, which, for example, can be assembled around an engine and fan assembly such as engine 108 and cooling fan 110. As noted above, acoustic liner 200 is typically oriented with an inner (i.e., concave) perforated facesheet to suppress engine and fan noise in area A. It will be appreciated that other acoustic liner configurations (e.g., inner duct wall 112B in FIG. 1) may have outer (i.e., convex) perforated facesheets, depending on the application configuration. Moreover, it will also be appreciated that the shape and size of an acoustic liner can take many different forms, as determined by a particular noise suppression application. The exemplary configuration of acoustic liner 200, as depicted in FIG. 2, is used herein as merely one example of a convenient shape to aid in the description of a repositionable mask.

Figure 3:
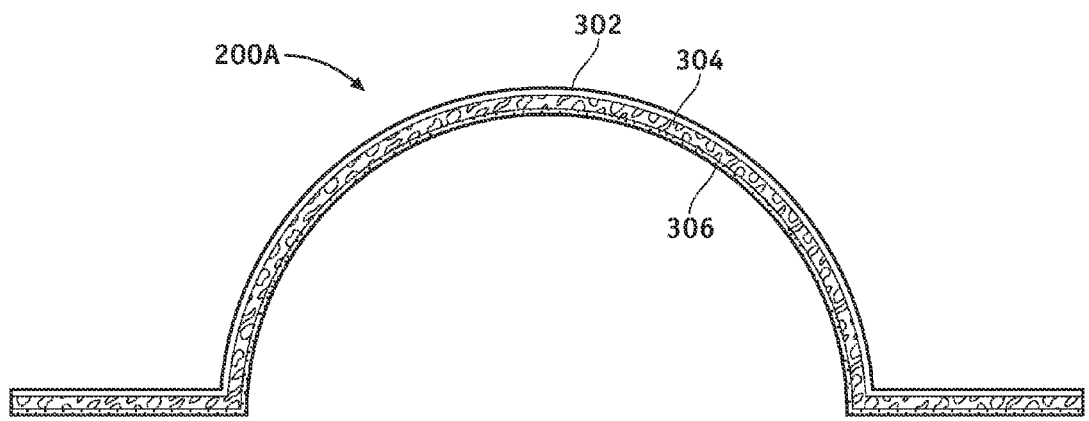
FIG. 3 is a cross-sectional illustration of an exemplary acoustic liner having a perforated face sheet.

A typical cross-section of acoustic liner part 200A is illustrated in simplified form in FIG. 3. In this example, an outer layer 302 is shown as a solid backsheet covering the outer surface of an interior section 304, which is typically fabricated in a honeycomb configuration for sound absorption. An exemplary inner layer 306 represents a perforated facesheet covering the inner surface of interior honeycomb section 304. A typical perforated facesheet configuration might include a number of holes of approximately 0.04 inch in diameter spaced approximately 0.1 inch apart, such that about 5% to 15% of the total surface of the perforated facesheet is open.

As noted above, acoustic liners are commonly inspected with TTU squirter systems, as will be described more fully below. However, if water from a TTU squirter system enters an acoustic liner honeycomb structure through a perforated facesheet, significant processing problems can occur during the subsequent finishing operations. For example, the paints and surface filling compounds typically used can be fouled from water vapor evolving from the structure during baking operations. To avoid this type of problem, the entire perforated area of the acoustic liner assembly is typically masked to prevent water ingression. The masking material is generally in intimate contact with the skin surface to allow the ultrasonic inspection signal to pass through. A conventional masking material (e.g., an adhesive coated tape material) is typically applied in a laborious manual process, in order to avoid the entrapment of air or wrinkles during the application process. The presence of voids or disbands in the mask-to-skin interface may cause interference with ultrasonic transmissions through the acoustic liner, and may lead to the misinterpretation of data.

Due to the typical compound contours and possible surface imperfections of acoustic liners, the masking material adhesive is generally selected with relatively aggressive tack characteristics, so that the mask can remain fully conforming to the liner surface. Once the mask is adhered to a liner surface (i.e., a perforated facesheet), it is generally desirable for the mask to maintain full contact with the liner surface during TTU inspection and other related procedures that may range in time to approximately 48 hours. It is also generally desirable that the mask adhesion characteristics are not adversely affected by seasonal room temperature changes within an inspection environment.

Another desirable property for a mask adhesive is relative ease of removal from a liner surface after the completion of a TTU inspection. While conventional taping materials can generally be removed after inspection, the taping process can be labor-intensive and time-consuming, especially for relatively large test articles such as aircraft acoustic liners. Moreover, residue from the taping materials often remains on the liner surface after removal, further complicating the process. In addition, conventional taping materials are routinely discarded after one application and removal, thereby representing a production cost consideration.

Figure 4:
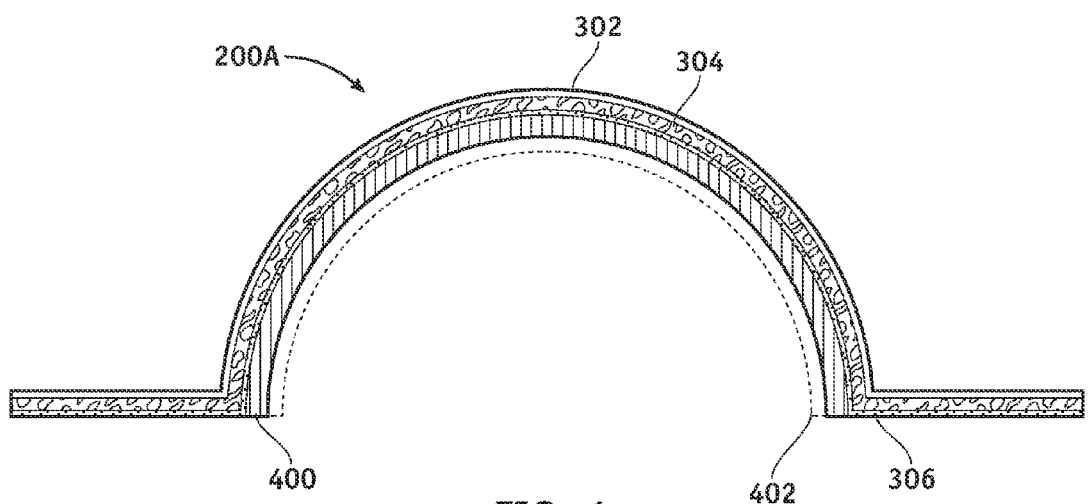
FIG. 4 is a cross-sectional illustration of an exemplary embodiment of an acoustic liner with a repositionable mask for protecting the perforated face sheet.

Because of the disadvantageous characteristics of conventional masking tape materials as described above, a different approach to masking a perforated facesheet is disclosed herein that replaces the conventional multi-strip tape procedure with a single-piece mask material. According to an exemplary embodiment of acoustic liner portion 200A with a single-piece mask 400, as shown in FIG. 4, a single sheet of pressure sensitive adhesive (PSA) is formed into mask 400 with a size and shape to cover the holes in perforated facesheet 306 of acoustic liner 200A. PSA mask 400 can be cast from a hot-melt adhesive or can be fabricated by extrusion. One example of a suitable hot-melt adhesive is an ethylene vinyl acetate (EVA) copolymer with approximately 50% vinyl acetate (VA) content. Other types or combinations of PSAs may also be used, depending on the adhesive characteristics (tack level) desired. The tack level of exemplary EVA mask 400 can be adjusted in order to provide sufficient adhering strength in combination with adequate removal characteristics. For example, the tack level can be adjusted by modifying the molecular weight or the VA content of the material in mask 400. The properties of mask 400 material can also be adjusted by compounding the material with fillers, or by blending the material with other polymers.

In general, an EVA copolymer with approximately 50% VA content remains permanently tacky at room temperature without the use of solvents. Moreover, since EVA is a polymer, the tack level of the material is generally unaffected by material aging or by typical changes in room temperature. In addition, an EVA mask can generally be removed from a facesheet surface by peeling, and without leaving a residue. Furthermore, EVA masks do not typically contaminate the masked surface, and EVA masks generally do not exude residues upon aging.

Referring again to FIG. 4, an exemplary embodiment of EVA mask 400 is adhered to perforated facesheet 306 on acoustic liner 200A. As will be described below, exemplary EVA mask 400 is typically configured to protect honeycomb structure 304 from water leakage through the perforations in facesheet 306 during a TTU squirter system inspection. In certain applications, mask 400 may be mounted within a contoured frame (not shown), to minimize sagging or stretching of the masking material during application and removal. When a frame is employed, the design of the frame should be configured to avoid interference with the ultrasonic transmission of a TTU inspection process.

In an alternative exemplary embodiment, mask 400 may be constructed with a backing 402, herein designated as a "carrier" for ease in handling, and shown in dashed line form in FIG. 4. In this embodiment, a sheet of EVA PSA (400) having a thickness in the approximate range of about 0.03 to 0.08 inch is typically applied to a thermoformed acrylic or polycarbonate carrier (402) to form a mask/carrier combination prior to application to facesheet 306. The overall thickness of mask 400 and carrier 402 is typically limited (e.g., to an approximate maximum thickness of 0.14 inch) in order to minimize interference with the ultrasonic signal used in TTU inspections. A suitable carrier 402 for this type of application is generally configured as a semi-rigid pre-contoured backing, with sufficient strength and compliance to permit associated mask 400 to be peeled from facesheet 306 after completion of the TTU inspection. As such, the bond strength of mask 400 to carrier 402 is typically greater than the bond strength of mask 400 to facesheet 306. These relative bond strengths can be controlled through the judicious selection of carrier material and bonding characteristics of the mask.

Figure 5:
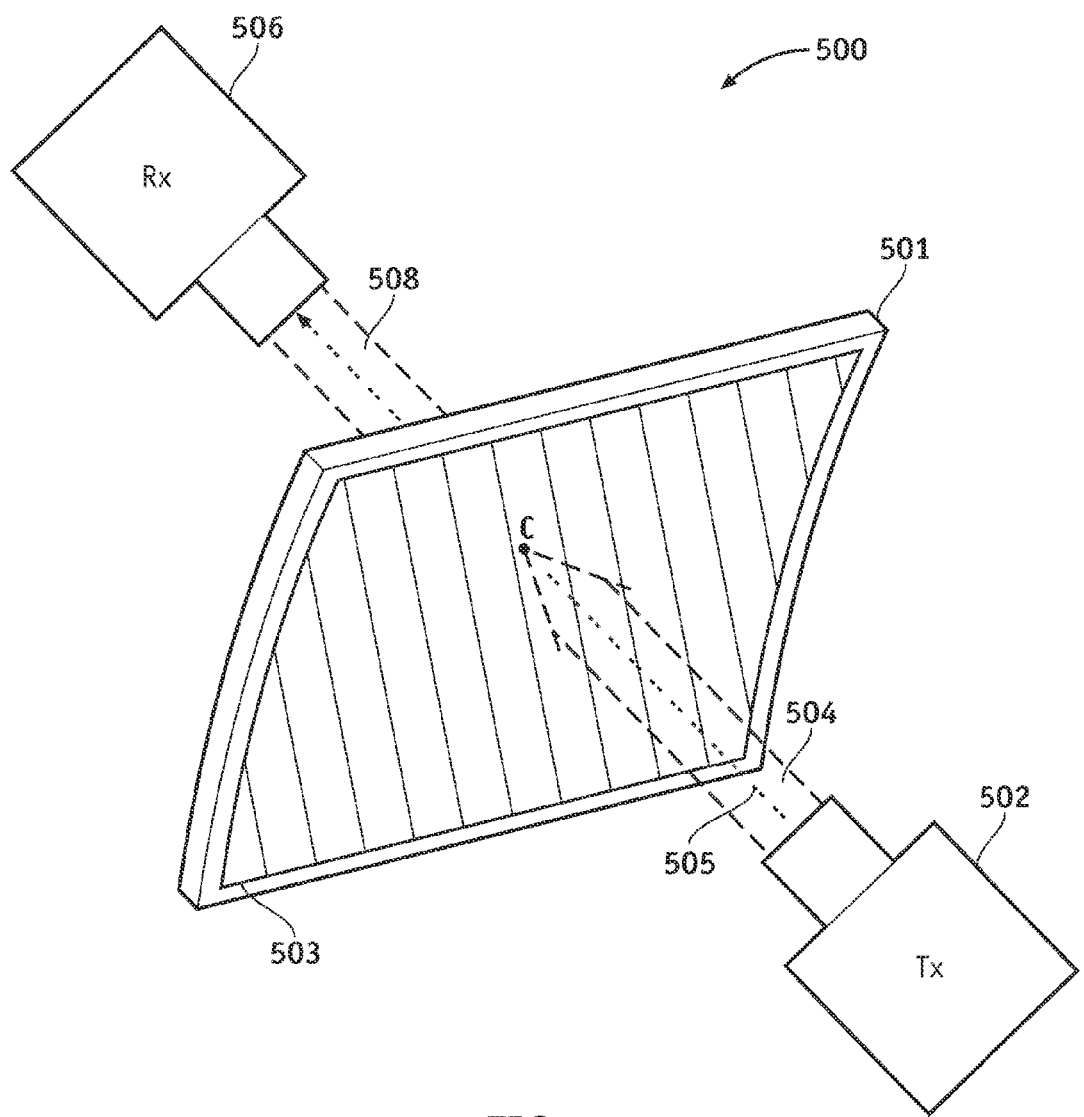
FIG. 5 is an illustration of an exemplary embodiment of an ultrasonic squirter system TTU inspection arrangement.

A typical TTU inspection arrangement 500 is depicted in FIG. 5 for an acoustic liner part 501 (similar in construction to liner 200A) and a protective mask 503 (similar in construction to mask 400). A squirter system transmitter 502 generates an ultrasonic beam 505 along a water stream 504 that impinges on the surface of mask 503 at a point C. As noted previously, mask 503 prevents moisture from water stream 504 from entering the internal honeycomb section of acoustic liner part 501 via the holes in the perforated facesheet of acoustic liner part 501 (not shown). Simultaneously, a squirter system receiver 506 generates a water stream 508 that impinges on the solid backsheet of acoustic liner part 501 in precise alignment with water stream 504. Ultrasonic beam 505 passes through mask 503 and acoustic liner part 501, and continues along water stream 508 to receiver 506, where it is converted to output data. Typically, an ultrasonic squirter system acquires data from a universe of scanned points across the body of a test part (501 in this example) and then processes the data to determine the inspection results. This type of system is commercially available from sources such as Boeing Automated Systems in St. Louis, Mo.

Accordingly, the shortcomings of the prior art have been overcome by providing an improved mask for TTU squirter system inspection applications. Exemplary embodiments of a repositionable mask are disclosed herein that protect an acoustic liner with a perforated facesheet from the water streams typically used in TTU squirter system inspections. The exemplary repositionable mask is generally fabricated from an EVA material with adhesion properties that enable the mask to adhere intimately to the liner surface to be protected, and also to be removable from the liner surface with minimal adverse effects on either the mask or the liner. As such, the mask can be repositioned (reused) on other liners for subsequent testing.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing the exemplary embodiment or exemplary embodiments. It should be understood that various changes can be made in the function and arrangement of elements without departing from the scope of the invention as set forth in the appended claims and the legal equivalents thereof.

What is claimed is:

1. A system for through-transmission ultrasonic (TTU) inspection of an article, comprising:
   an ultrasonic squirter system configured to supply a water-transported ultrasonic signal through the article;
   a repositionable mask configured to cover one or more surfaces of the article, wherein the repositionable mask protects and adheres to the one or more surfaces of the article from the water stream generated by the ultrasonic squirter system, and wherein the repositionable mask is configured to be removed from the one or more surfaces and reused for subsequent TTU inspections.

2. The system of claim 1 wherein the repositionable mask is substantially in full and intimate contact with the one or more surfaces of the article.

3. The system of claim 1 wherein the repositionable mask can adhere to the one or more surfaces of the article for a time period of up to approximately 48 hours.

4. The system of claim 1 wherein the repositionable mask is non-residue producing.

5. The system of claim 1 wherein the repositionable mask is removed by peeling.

6. The system of claim 1 wherein the repositionable mask is fabricated from an ethylene vinyl acetate copolymer.

7. The system of claim 6 wherein the ethylene vinyl acetate copolymer includes approximately 50% vinyl acetate content.

8. The system of claim 1 wherein the repositionable mask further comprises an integrated backing material carrier.

9. The system of claim 8 wherein the integrated backing material carrier is configured as a semi-rigid pre-contoured carrier.

10. The system of claim 9 wherein the semi-rigid pre-contoured carrier is fabricated from thermoformed acrylic.

11. The system of claim 9 wherein the semi-rigid pre-contoured carrier is fabricated from thermoformed polycarbonate.

12. A method of inspecting articles using squirter system through-transmission ultrasonic (TTU) inspection, the method comprising:
   adhering a pressure sensitive adhesive mask on a surface of a first article;
   inspecting the first article with the pressure sensitive adhesive mask adhered thereto;
   removing the pressure sensitive adhesive mask from the first article; and
   adhering the pressure sensitive adhesive mask on a surface of a second article.

13. The method of claim 12, further comprising inspecting the second article with the pressure sensitive adhesive mask adhered thereto.

14. The method of claim 13, wherein inspecting the first article and inspecting the second article utilizes squirter system TTU inspection.

15. The method of claim 12, wherein:
   inspecting the first article is performed by an ultrasonic squirter system configured to supply a water-transported ultrasonic signal through the first article; and adhering the pressure sensitive adhesive mask covers the surface of the first article to protect the surface from a water stream generated by the ultrasonic squirter system.

16. The method of claim 12, wherein adhering the pressure sensitive adhesive mask comprises placing the pressure sensitive adhesive mask into substantially full and intimate contact with the surface of the first article.

17. The method of claim 12, wherein removing the pressure sensitive adhesive mask comprises peeling the pressure sensitive adhesive mask intact from the surface of the first article.

18. The method of claim 12, wherein:
the first article comprises a perforated facesheet and an interior structure covered by the perforated facesheet;
adhering a pressure sensitive adhesive mask comprises adhering the pressure sensitive adhesive mask on the perforated facesheet, the pressure sensitive adhesive mask preventing water dispensed during the TTU inspection from entering the interior structure of the first article through the perforated facesheet.

19. A method of ultrasonically inspecting an article, the method comprising:
adhering a pressure sensitive adhesive mask on a first surface of the article;
performing squirter system through-transmission ultrasonic (TTU) inspection on the article with the pressure sensitive adhesive mask adhered to the first surface;
removing the pressure sensitive adhesive mask from the first surface;
adhering the pressure sensitive adhesive mask on a second surface of the article; and
performing squirter system TTU inspection on the article with the pressure sensitive adhesive mask adhered to the second surface.

20. The method of claim 19, wherein:
adhering the pressure sensitive adhesive mask on the first surface comprises placing the pressure sensitive adhesive mask into substantially full and intimate contact with the first surface;
removing the pressure sensitive adhesive mask from the first surface comprises peeling the pressure sensitive adhesive mask intact from the first surface; and
adhering the pressure sensitive adhesive mask on the second surface comprises placing the pressure sensitive adhesive mask into substantially full and intimate contact with the second surface.

* * * * *